US008290815B2

(12) United States Patent
Heere et al.

(10) Patent No.: US 8,290,815 B2
(45) Date of Patent: Oct. 16, 2012

(54) IMAGE ARCHIVING AND COMMUNICATIONS SYSTEM

(75) Inventors: Edward C. Heere, Redding, CT (US); Roger S. Metz, Sandy Hook, CT (US)

(73) Assignee: CoActiv, LLC, Ridgefield, CT (US)

( * ) Notice: Subject to any disclaimer, the term of this patent is extended or adjusted under 35 U.S.C. 154(b) by 1932 days.

(21) Appl. No.: 10/982,860

(22) Filed: Oct. 28, 2004

(65) Prior Publication Data

US 2005/0148849 A1 Jul. 7, 2005

Related U.S. Application Data

(60) Provisional application No. 60/515,353, filed on Oct. 29, 2003.

(51) Int. Cl.
*G06Q 10/00* (2012.01)
(52) U.S. Cl. .................................. 705/20; 705/2; 705/3
(58) Field of Classification Search ...................... 705/20
See application file for complete search history.

(56) References Cited

U.S. PATENT DOCUMENTS

| | | | |
|---|---|---|---|
| 4,642,621 A | 2/1987 | Nemoto et al. ............... 340/721 |
| 4,893,270 A | 1/1990 | Beck et al. ..................... 364/900 |
| 5,019,976 A | 5/1991 | Chiu et al. ................. 364/413.13 |
| 5,204,947 A | 4/1993 | Bernstein et al. ............. 395/157 |
| 5,272,760 A | 12/1993 | Echerer et al. ...................... 382/6 |
| 5,293,313 A | 3/1994 | Cecil et al. ................ 364/413.22 |
| 5,313,567 A | 5/1994 | Civanlar et al. ............... 395/124 |
| 5,452,416 A | 9/1995 | Hilton et al. .................. 395/161 |
| 5,920,317 A | 7/1999 | McDonald ..................... 345/356 |
| 6,081,267 A | 6/2000 | Stockham et al. ............. 345/342 |
| 6,128,002 A | 10/2000 | Leiper ........................... 345/156 |
| 6,177,937 B1 | 1/2001 | Stockham et al. ............. 345/340 |
| 6,184,862 B1 | 2/2001 | Leiper ........................... 345/156 |
| 6,256,613 B1 * | 7/2001 | Falchuk et al. .................... 705/2 |
| 6,269,379 B1 | 7/2001 | Hiyama et al. ................. 707/104 |
| 6,272,470 B1 * | 8/2001 | Teshima ............................. 705/3 |
| 6,392,633 B1 | 5/2002 | Leiper ........................... 345/161 |
| 6,469,717 B1 | 10/2002 | Wineke et al. ................. 345/788 |
| 6,518,952 B1 | 2/2003 | Leiper ........................... 345/156 |
| 6,678,764 B2 * | 1/2004 | Parvulescu et al. ............. 710/65 |
| 2002/0080392 A1 | 6/2002 | Parvulescu et al. |
| 2002/0128873 A1 * | 9/2002 | Shimizu et al. .................... 705/3 |
| 2002/0152096 A1 * | 10/2002 | Falchuk et al. .................... 705/2 |
| 2006/0122482 A1 * | 6/2006 | Mariotti et al. ............... 600/407 |

OTHER PUBLICATIONS

Web Dominator™ Radiologist's Remote Reading Station. DR Systems' Mission is to Enhance the Clinical and Financial Success of our Medical Imaging Customers.
Canadian Office Action; Application No. 2486016; Jul. 30, 2009; 4 pages.

* cited by examiner

*Primary Examiner* — Hiep V Nguyen
(74) *Attorney, Agent, or Firm* — St. Onge Steward Johnston & Reens LLC

(57) ABSTRACT

A system for facilitating the communication of images includes a central computer and at least one remote computer in communication with the central computer via a communication link. Computer executable instructions executing on the at least one remote computer automatically and without user input determine whether an image is available for download from the central computer, and if an image is available for download from the central computer, automatically and without user input download the image in the background. Additional computer executable instructions executing on the at least one remote computer, after the download of the image is completed, generate and cause to be displayed a notification that the image is ready for display. Further computer executable instructions executing on the at least one remote computer, in response to a request to display the downloaded image, cause the image to be displayed.

29 Claims, 4 Drawing Sheets

IMAGE ARCHIVING AND COMMUNICATIONS SYSTEM

RELATED APPLICATIONS

This patent application claims the benefit of, under Title 35, United States Code, Section 119(e), U.S. Provisional Patent Application No. 60/515,353, filed Oct. 29, 2003.

FIELD OF THE INVENTION

The present invention relates to the storage, retrieval, display and communication of images, such as medical images, and more particularly to a system for facilitating the communication of images in a digital format between various individuals and/or entities.

BACKGROUND OF THE INVENTION

Medical technology has created the expectation that there be an ability to "instantly" transmit critical patient clinical and demographic information between medical and other healthcare entities. A surgeon or other specialist is often waiting for critical patient clinical information in order to make potentially life saving decisions regarding a patient's immediate medical care. Often this clinical information is requested to be sent "stat", the term meaning that the information is being required immediately to make medical treatment decisions.

In the case of many electronic format medical images, such as radiological images, the large data files are can take significant lengths of time to electronically transmit to the treating physician's location. Also, Health Insurance Portability and Accountability Act of 1996 (HIPAA) regulations, as well as proper professional practice, demand that this information be transmitted in a manner that maintains patient privacy and in a manner that assures that the data is securely and reliably transmitted, all without compromising the need to transmit the data as soon as possible.

There are numerous challenges in the implementation of such systems. Although broadband digital connectivity is becoming more readily available, and at affordable costs, this connectivity is usually not secure, sometimes unreliable, and in many cases still too expensive to utilize and still allow a medical practice to operate profitably in the current era of diminishing health maintenance organization (HMO) reimbursements and skyrocketing medical insurance costs. There exists an immediate need for a healthcare entity-to-healthcare entity communications solution that meets the following requirements.

This solution should preferably be: (i) secure enough to meet both HIPAA privacy and security guidelines; (ii) fast enough to deliver data to meet "stat" demands; (iii) reliable enough to assure delivery at any time or day of the week; (iv) affordable enough for even the smallest medical practice in the most economically depressed areas of the country; (v) easy to install, maintain and monitor so that practices without information technology (IT) departments can utilize the system without taking on the additional costs of staff technology employees or having to purchase expensive outside technology support; (vi) robust enough to allow the medical practitioners to feel comfortable that the transmission method will provide reliable medical data delivery; (vii) "technology flexible" in order to allow for and utilize the various types of data connectivity that are regionally available including, but not limited to, digital subscriber lines (DSL), cable modem services, fractional and full bandwidth frame relay lines, integrated services digital network (ISDN) lines, point-to-point direct connect lines, satellite based communication services (e.g., those offered by Hughes Digital), dial-up services (although usually too slow for efficient larger digital image transmissions), and other services currently available and planned for the near future; (viii) easily upgradeable to accommodate newer and faster connectivity as it evolves with a minimal amount of technological obsolescence; (ix) based on non-proprietary and easily available proven transmission technologies; and (x) flexible enough to accommodate all types of healthcare related information and data including, but not limited to all size and format radiological Digital Imaging and Communications in Medicine (DICOM) standard images and other digital exam studies and images, all digital medical images from, and/or for, all medical specialties, digital video studies and reports as required, medical reports, dictated voice files in wave, MP3 and other formats, scanned patient information such as insurance cards, prescriptions, and all other pertinent patient data, insurance records and capitation information, medical histories and other historical, medical and demographic information, and virtually any information that needs to be moved from healthcare entity to healthcare entity in a manner that meets all of the above required restrictions. There currently exists no system which satisfies all of the above needs.

One example of a field which relies upon medical images is the radiology field. In the past, if a referring physician needed to view a patient's radiological exam images on a "stat" basis, the method of getting these images to the doctor followed an antiquated procedure which included; producing additional copies of hard-film X-rays, CT or MRI images (an expensive process) and sending them via messenger or courier service (another expensive process) from the imaging center to the doctor's office. If the two locations were in the same neighborhood, this procedure was often the only solution, and it has been used for years. If the two locations were distant, an overnight courier service (also expensive) was utilized.

The recent conversion of many radiology imaging centers from film-based modalities to digital DICOM compliant modalities now allows for the creation of digital radiological images. While less expensive to produce and manage than film, these digital images and studies must somehow still be delivered to the referring physician in a speedy and cost effective manner. Current technology has permitted the development of two new improved methods of moving this medical information, both of which have addressed only some of the earlier issues and concerns.

The first method entails the producing of a CD containing the patient's images and usually some type of viewer that can then be used by the referring physician to view and analyze these images. It is far less expensive and much quicker to burn an exam CD for less than $1.00 than it is to produce copies of hard-film studies. It is also much more convenient for the doctor to file the small CD in the patient's file jacket than it is to store large, cumbersome and bulky film studies. However, the problem of speedy delivery to the referring physician still exists and is currently solved by the traditional method of courier, messenger or overnight delivery service.

The second new method of making the radiological information available to referring physicians entails making the images (and sometimes other information) available on a web-based server and then giving the doctor the ability to securely login and view this information from a remote location. U.S. Pat. No. 5,920,317 to McDonald discloses such a system and method for storing and displaying ultrasound images. The system includes a networked series of computers 26, 22, 24 with ultrasound images being stored on a server side in a compact disk changer/player 28. The ultrasound images may be accessed and viewed through an ultrasound image review module executing on a remote computer 26 in communication with the server 24 through a WAN 34, such as the Internet. Another of these types of systems is distributed by DR Systems, Inc. under the name "Web Dominator". The "Web Dominator" is a software product which allows a PC to be used as a remote terminal which allows for the downloading of exam images via VPN or SSL.

While these systems and methods address some of the existing concerns, such as potentially dealing with the speedy delivery issue (depending on the doctor's Internet connection speed), they do so at an often-unacceptable cost in other areas. All of these systems operate by allowing a user to log on to a server via a communications link and then to request download of desired images. Even when the user has a fast communications link, however, due to the often huge size of the images, download can take a significant amount of time. It is, of course, possible to compress these web-published images in order to make them smaller so as to speed download time. However, in order to make download time acceptable, the images typically must be compressed to a degree that makes them of too low a resolution to perform a primary diagnostic read. While this is sometimes acceptable, since the referring doctor sometimes depends on the diagnostic radiologist to perform this function and only requires the images for referral purposes or to show to a patient, it is obviously not an optimal solution. Certain specialties, such as orthopedic surgeons, cardiologists, neurosurgeons and some others usually require the high-resolution original radiological images to perform their procedures with any level of confidence.

As such, what is desired is a system which does not require a user to choose between waiting for an extended period while an image downloads or sacrificing image quality. More specifically, what is desired is a system which provides high quality, images to a user without requiring compression resulting in image degradation and without requiring that a user request to view an image and then wait an unreasonably long time for the requested image to be downloaded.

SUMMARY OF THE INVENTION

Accordingly, it is an object of the present invention to provide a system for facilitating the communication of images which communicates high quality and high resolution images.

Another object of the present invention is to provide a system for facilitating the communication of images having the above characteristics and which communicates images without requiring compression resulting in image degradation.

A further object of the present invention is to provide a system for facilitating the communication of images having the above characteristics and which does not require that a user wait for an extended period of time for an image to be downloaded after requesting the image.

These and other objects of the present invention are achieved in accordance with one embodiment of the invention by provision of a system for facilitating the communication of images, the system including a central computer and at least one remote computer in communication with the central computer via a communication link. Computer executable instructions executing on the at least one remote computer automatically and without user input determine whether an image is available for download from the central computer, and if an image is available for download from the central computer, automatically and without user input download the image in the background. Additional computer executable instructions executing on the at least one remote computer, after the download of the image is completed, generate and cause to be displayed a notification that the image is ready for display. Further computer executable instructions executing on the at least one remote computer, in response to a request to display the downloaded image, cause the image to be displayed.

In some embodiments, the central computer comprises an imaging center computer. In some embodiments, the at least one remote computer comprises a referring physician computer. In certain of these embodiments, the at least one remote computer further comprises a consulting physician computer, and computer executable instructions executing on the consulting physician computer determine that an image is available for download only if a request that the image be shared with the consulting physician computer is received from the referring physician computer.

In some embodiments, the image comprises a medical image file plus at least one appended data file. In certain of these embodiments, the medical image file comprises a Digital Imaging and Communications in Medicine (DICOM) standard image. In some embodiments, status of the image download by the remote computer is visible to a user of the remote computer, while in some embodiments, status of the image download by the remote computer is invisible to a user of the remote computer. In some embodiments, the system further comprises an archive for long-term storage of the image. In some embodiments, the at least one remote computer comprises a removable storage device onto which the image may be saved.

In some embodiments, the computer executable instructions executing on the at least one remote computer automatically and without user input determine whether an image is available for download from the central computer by automatically and without user input polling the central computer periodically or from time-to-time to determine whether an image is available for download. In some embodiments, the computer executable instructions executing on the at least one remote computer automatically and without user input determine whether an image is available for download from the central computer by automatically and without user input receiving an indication that an image is available for download from the central computer.

In accordance with another embodiment of the present invention, a system for facilitating the communication of medical images from an imaging center to at least one physician includes an imaging center computer and a referring physician computer in communication with the imaging center computer via a communication link. Computer executable instructions executing on the referring physician computer automatically and without user input poll the imaging center computer periodically or from time-to-time to determine whether an image is available for download, and if an image is available for download from the imaging center computer, automatically and without user input download the image in the background. Additional computer executable instructions executing on the referring physician computer, after the download of the image is completed, generate and cause to be displayed a notification that the image is ready for display. Further computer executable instructions executing on the referring physician computer, in response to a request to display the downloaded image, cause the image to be displayed.

In some embodiments, the system further includes a consulting physician computer in communication with the imaging center computer via a communication link. Computer executable instructions executing on the consulting physician computer automatically and without user input poll the imaging center computer periodically or from time-to-time to determine whether an image is available for download, and if an image is available for download from the imaging center computer, automatically and without user input download the image in the background. Additional computer executable instructions executing on the consulting physician computer, after the download of the image is completed, generate and cause to be displayed a notification that the image is ready for display. Further computer executable instructions executing on the consulting physician computer, in response to a request to display the downloaded image, cause the image to be displayed. In certain of these embodiments, the computer executable instructions executing on the consulting physician computer determine that an image is available for download only if a request that the image be shared with the consulting physician computer is received from the referring physician computer.

In some embodiments, the image comprises a medical image file plus at least one appended data file. In certain of these embodiments, the medical image file comprises a Digital Imaging and Communications in Medicine (DICOM) standard image. In some embodiments, status of the image download by the referring physician computer is visible to a user of the referring physician computer, while in other embodiments, status of the image download by the referring physician computer is invisible to a user of the referring physician computer. In some embodiments, the system further includes an archive for long-term storage of the image. In some embodiments, the referring physician computer comprises a removable storage device onto which the image may be saved.

In accordance with another aspect of the present invention, a method for facilitating the communication of images comprises the steps of: (i) determining, automatically and without user input, whether an image is available for download from a central computer; (ii) downloading, if it is determined that an image is available for download, the image in the background of a computer operating system automatically and without user input; (iii) notifying, after the download is completed, a user that the image is available for viewing; (iv) receiving a request for display of the image from the user; and (v) displaying the image to the user.

In some embodiments, the central computer comprises an imaging center computer. In some embodiments, the downloading, the notifying, the receiving, and the displaying steps are performed by a referring physician computer. In certain of these embodiments, the method further comprises the steps of: (vi) receiving, with the central computer, an indication from the referring physician computer that the image should be shared with a consulting physician computer; (vii) making the image available for download by the consulting physician computer; and (viii) performing the downloading, the notifying, the receiving, and the displaying steps with the consulting physician computer. In certain embodiments, status of the downloading step is visible to a user of the referring physician computer, while in some embodiments, status of the downloading step is invisible to a user of the referring physician computer.

In some embodiments, the determining step comprises the step of automatically and without user input polling a central computer periodically or from time-to-time to determine whether an image is available for download. In some embodiments, the determining step comprises the step of automatically and without user input receiving an indication that an image is available for download from the central computer.

The invention and its particular features and advantages will become more apparent from the following detailed description considered with reference to the accompanying drawings.

DETAILED DESCRIPTION OF AN EMBODIMENT OF THE INVENTION

Figure 1:
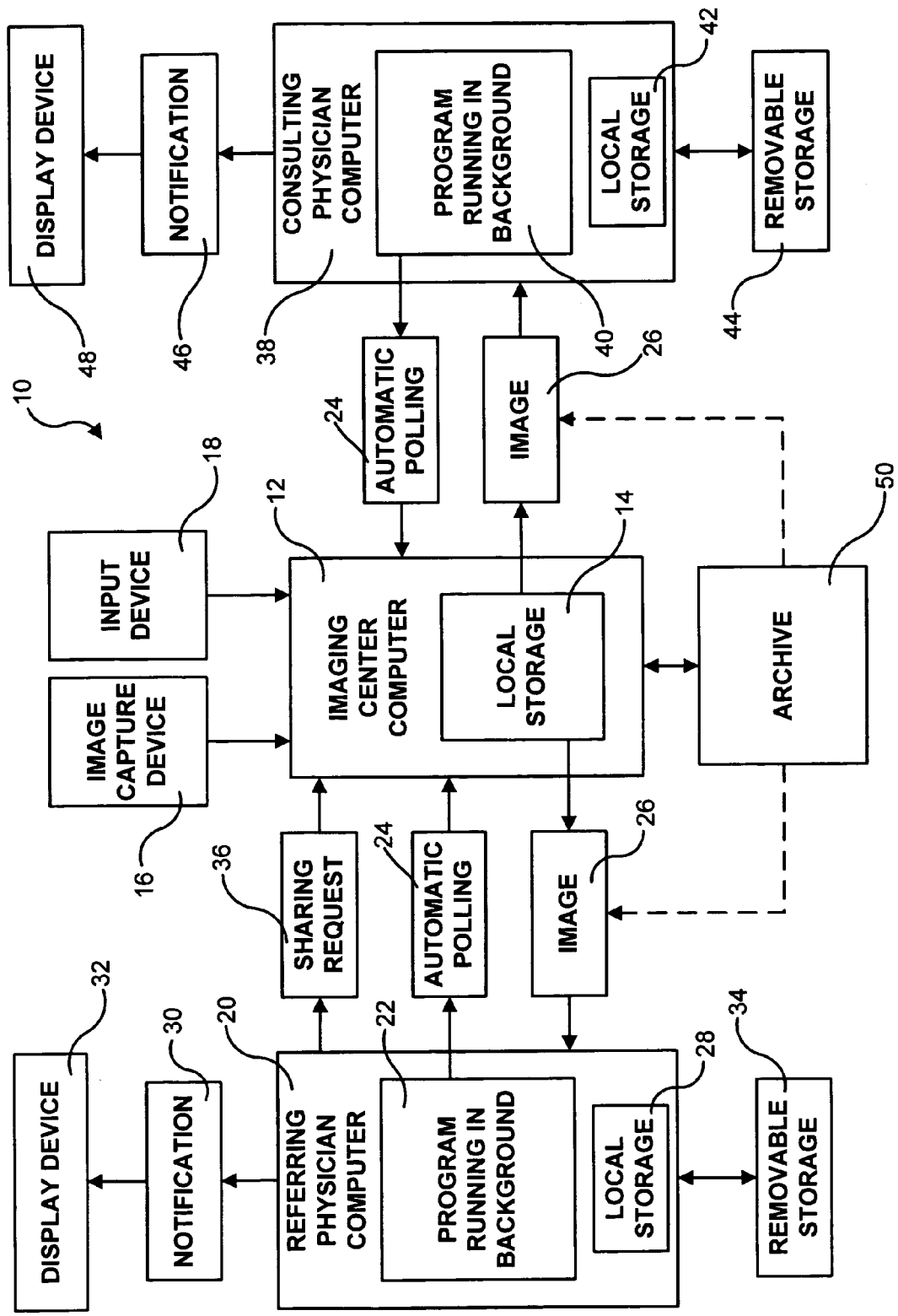
FIG. 1 is a block diagram illustrating a system for facilitating the communication of images in accordance with one embodiment of the present invention.

Referring first to FIG. 1, a system 10 for facilitating the communication of images in accordance with an embodiment of the present invention is shown. The system 10 includes an imaging center computer 12, which may be located at the imaging center where images are taken or may be located remotely therefrom. Imaging center computer 12 may be a server, and preferably is associated with a local storage device 14 for storing images thereon, at least on a short-term basis (as described more fully below). The images are acquired by an image capture device 16, which may employ any of various still image techniques, such as X-ray, CT scan, MRI, etc., or it may employ techniques which produce digital video images, such as those produced by ultrasound, nuclear scans, etc. System 10 also includes, at least one additional input device 18 by which the physician evaluating the images (usually a radiologist) may modify the image (such as by inserting markers therein), may record a report (for example, by typing it into a computer, by creating a voice recording, etc.) and append it to the image, may enter patient information and append it to the image, or may modify the image or append further information to the image in some other way.

System 10 also includes a referring physician computer 20 which is in communication with imaging center computer 12 via a communications link. The communications link may take substantially any form, and may be dictated by the types of technology that are available in various parts of the country or the world. Some examples of the technologies which may be employed for the communications link include, but are not limited to, DSL, cable modem services, fractional and full bandwidth frame relay lines, ISDN lines, point-to-point direct connect lines, satellite based communication services, dial-up services (although usually too slow for efficient larger digital image transmissions), and other services currently available or that are later developed.

There is running in the background on referring physician computer 20 a program 22. By "running in the background", what is meant is that program 22 is operating on referring physician computer 22 without requiring user input and without interfering with other programs which the referring physician may be operating. Program 22 may be visible to the user in that the referring physician may be able to view the status of program 22 as it is running (i.e., the referring physician may be able to see when an image is being downloaded, as described in more detail below), or program 22 may be invisible to the user (i.e., the referring physician cannot see that an image is being downloaded until the download is complete, also as described in more detail below).

Program 22 automatically polls 24 imaging center computer 12 via the communications link periodically or from time-to-time in order to determine whether there is waiting on imaging center computer 12 (for instance in local storage 14) an image waiting to be downloaded. As discussed above, there may be additional files appended to the image, but for the sake of clarity, the image and any appended files are referred to herein as image 26. If there are one or more images ready to be downloaded, program 22 downloads the image 26 from imaging center computer 12. Depending upon the size of image 26 and the type of communications link between referring physician computer 20 and imaging center computer 12, this download process may take anywhere from a few seconds to several hours. The downloaded image 26 is stored on a local storage 28 on referring physician computer.

Preferably, the files associated with the image are uncompressed, or if compressed, are compressed in a lossless fashion, and comprise Digital Imaging and Communications in Medicine (DICOM) standard images. Also, in order to maintain patient confidentiality, the data files are encrypted, and a secure transmission method, such as Secure Socket Layer (SSL) web transmission, is employed.

Local storage 14 on imaging center computer 12 and local storage 28 on referring physician computer 20 may comprise substantially any kind of storage, such as RAM (usually only possible in the case of relatively small files), a hard disk drive, etc. If desired, local storage 14, 28 may comprise a redundant array of independent disks (RAID), a tape backup device, etc, although such is not strictly required, since images will typically only be stored on local storage 14, 28 for a relatively short duration, as discussed more fully below.

Once the image 26 has been completely downloaded, referring physician computer 20 generates a notification 30 indicative of such and transmits notification 30 to a display device 32 such that the referring physician is aware that an image is available for viewing. The display device 32 may simply comprise a monitor attached to referring physician computer 20, on which monitor the notification 30 is displayed. For example, the notification 30 may comprise a pop-up message displayed on the monitor. Alternately or in addition, the display device 32 may comprise a pager and the notification 30 may comprise a page sent to the pager, the display device 32 may comprise a wireless device such as a telephone, a PDA, a Blackberry® type device, etc., and the notification 30 may comprise a telephone call, an email or the like, the display device may comprise a computer separate from referring physician computer 20 and the notification 30 may comprise an email, etc.

While the particular physical embodiments of the display device 32 and the notification 30 are unimportant, what is important is that the program 22 notifies the referring physician after download is complete that the image 26 is available for viewing. Once the referring physician receives the notification 30, he/she may click on a user selectable indicia or the like displayed by referring physician computer 20, in response to which the image 26 is displayed. Since the image 26 has already been completely downloaded to referring physician computer 20, retrieving image 26 from local storage 28 and displaying image 26 to the referring physician is almost instantaneous even if the file was large and took a relatively long duration to download. Thus, there is virtually no wait time for the referring physician. Since the image 26 was downloaded in the background without any user input by the referring physician, and since the referring physician is only notified of the download after it has been completed, it appears to the physician that download of the image 26 is instantaneous.

Preferably, although not necessarily, referring physician computer 20 has associated therewith a removable storage device 34 on which the referring physician may save image 26. Removable storage device may comprise, for example, a CD burner, a DVD burner, a removable magnetic disk, etc. Thus, the referring physician may create a copy of image 26, for example, to provide a copy to the patient, to keep a copy in the patient's records, to provide a copy to a consulting physician if the consulting physician does not have the ability to receive images via system 10 (as explained more fully below), etc.

The referring physician also has the option, via referring physician computer 20, to request 36 that the image be shared with one or more consulting physicians. The selection of consulting physicians may be facilitated by providing a drop-down list or the like from which the referring physician may select. Of course, other means of selection are also possible, such as offering a search function, a favorites list or the like.

Each potential consulting physician has a consulting physician computer 38 which has a program 40 running in the background in the same manner as program 22 runs in the background on referring physician computer 20. Program 40 running on consulting physician computer 38, like program 20 running on referring physician computer 20, automatically polls 42 imaging center computer 12 via a communications link periodically or from time-to-time in order to determine whether there is waiting on imaging center computer 12 (for instance in local storage 14) an image waiting to be downloaded. While the image 26 in question may have been stored on imaging center computer for some time, it is not until imaging center computer 12 receives a sharing request 36 from the referring physician that the image 26 will be designated as waiting to be downloaded by the consulting physician. Thus, once the image 26 in question has been designated for sharing with the consulting physician, the next time program 40 running on consulting physician computer 38 polls 42 imaging center computer 12, download of the image 26 will commence.

Like referring physician computer 20, consulting physician computer 38 may have associated therewith a local storage device 42 and a removable storage device 44. Also, like program 22 running on referring physician computer 20, after download of the image 26 is completed, program 40 running on consulting physician computer 38 generates a notification 46 indicative of such, and transmits the notification 46 to a display device 48 in order to notify the consulting physician that an image is available for viewing.

If more than one consulting physician is specified by the referring physician, additional consulting physician computers preferably operate in the same manner as consulting physician computer 38.

System 10 may also include an archive 50 for the long-term storage of images. Archive 50 may comprise, for example, one or more RAIDs, one or more tape drives, one or more CD or DVD carousels, etc. Preferably, the archive 50 is located remotely from the imaging center computer 12 in case the location of the imaging center computer 12 is compromised in some fashion. Most preferably, archive 50 comprises two separate archives 50 which are located in separate facilities in case one of the facilities is compromised. By providing archive 50, it possible for images 26 to be stored on local storage 14 of imaging center computer 12 for only a short time. For example, images may be stored on local storage 14 for a few hours or a few days—just long enough for the images to be evaluated at the imaging center and transmitted to the referring physician. If the images are required again at a later date, they may be retrieved from archive 50.

Moreover, as indicated by dashed lines in FIG. 1, the image 26 downloaded to referring physician computer 20 and/or consulting physician computer 38 may be downloaded from archive 50, rather than from imaging center computer 12. This may be desirable, for example, where the mode of communications employed the imaging center computer 12 has a limited bandwidth, because rather than imaging center computer 12 being required to upload image 26 three times (i.e., once to the referring physician computer 20, once to the consulting physician computer 38 and once to the archive 50) or even more if more than one consulting physician is specified by the referring physician, imaging center computer 12 would only have to upload image 26 once (i.e., to the archive). It may also be desirable, for example, to keep the image 26 stored on local storage 14 of imaging center computer 12 just long enough for it to be downloaded by referring physician computer 20. In such case, if the referring physician later requests that the image be shared with a consulting physician, the image 26 may be downloaded by consulting physician computer 38 directly from archive 50.

Figure 2:
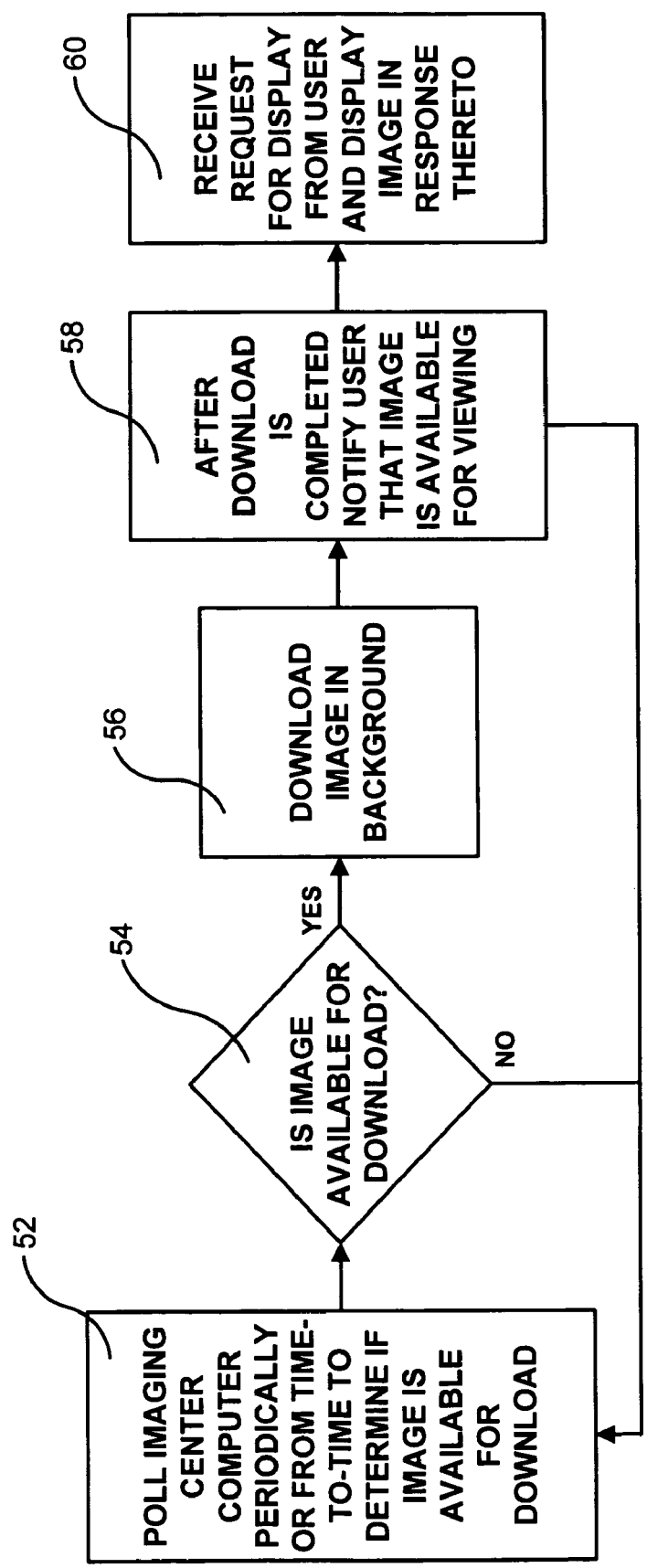
FIG. 2 is flow chart illustrating operation of the system for facilitating the communication of images shown in FIG. 1.

Referring now to FIG. 2, operation of program 22, 40 running on either referring physician computer 20 or consulting physician computer 38 in accordance with system 10 is shown in flow chart form. First, at step 52, program 22, 40 polls imaging center computer periodically or from time-to-time to determine whether an image is available for download. At decision block 54, if it is determined that no image is available for download, program 22, 40 continues to poll imaging center. However, if it is determined that an image is available for download, program 22, 40 downloads the image in the background at block 56. After the download is completed, program 22, 40 notifies the user (i.e., either the referring physician or the consulting physician) that an image is available for viewing at block 58. Program 22, 40 also goes back to polling the imaging center computer. Program 22, 40 then, after receiving a request for display of the image from the user (via a user selectable indicia for example) displays the image to the user at block 60.

Figure 3:
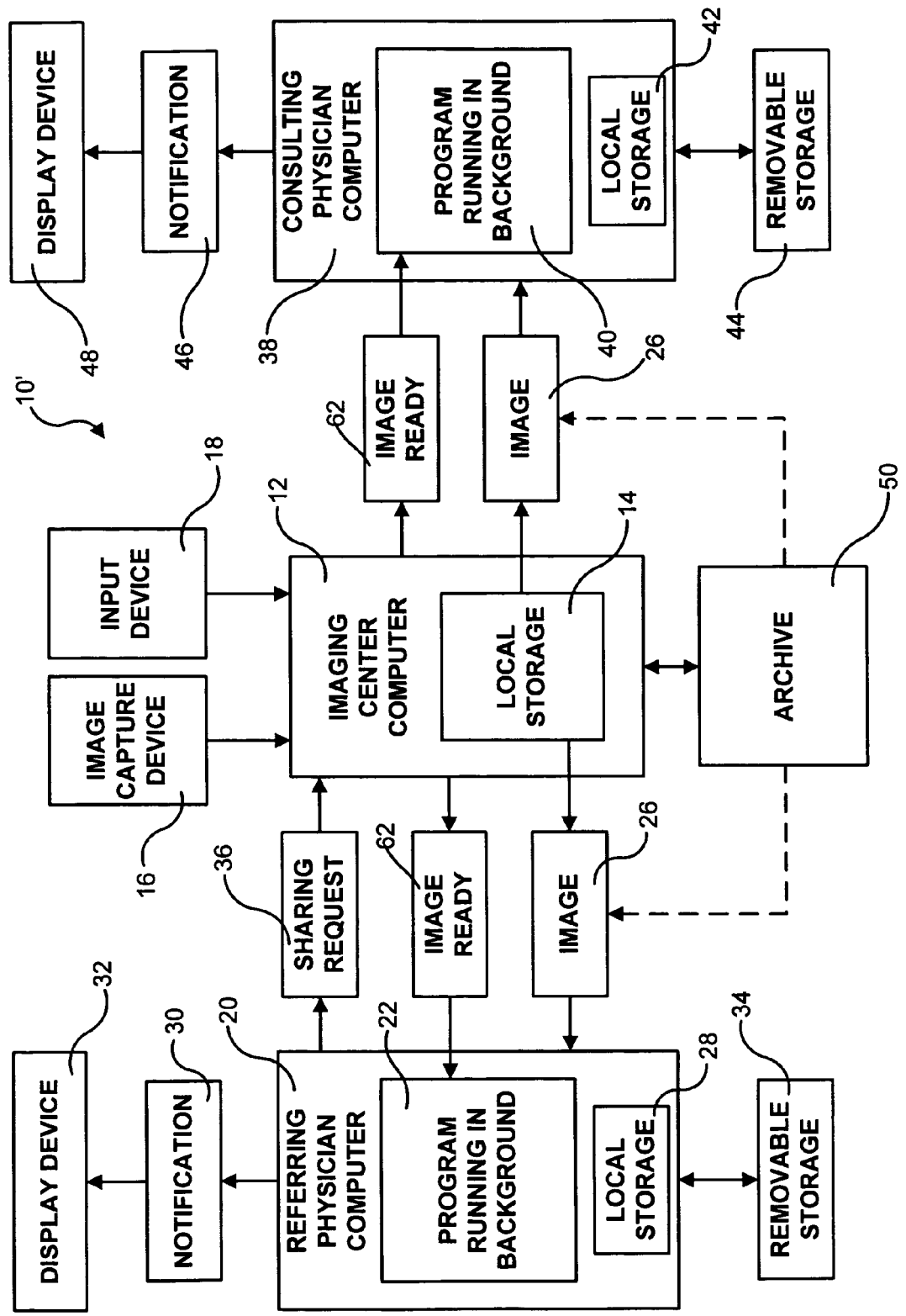
FIG. 3 is a block diagram illustrating a system for facilitating the communication of images in accordance with another embodiment of the present invention.

Referring now to FIG. 3, a system 10' for facilitating the communication of images in accordance with another embodiment of the present invention is shown. System 10' is similar to system 10 discussed above with respect to FIG. 1, and like elements are designated by like reference numbers. With respect to these elements, they are not discussed again with respect to FIG. 3 since they were fully discussed above.

The main difference between system 10' shown in FIG. 3 and system 10 shown in FIG. 1 is that whereas system 10 is a "pull" technology (in that images 26 are "pulled" from imaging center computer 12 by referring physician computer 20 and/or consulting physician computer 38), system 10' is a "push" technology, meaning that the images 26 are "pushed" from imaging center computer 12 to referring physician computer 20 and/or consulting physician computer 38. Thus, in system 10', programs 22, 40 do not poll imaging center computer 12 to determine whether images are ready for download. Instead, imaging center computer 12 notifies 62 programs 22, 40 running on referring physician computer 20 and consulting physician computer 38 when an image is ready for download, and automatically starts uploading images 26. Of course, this image transfer still occurs in the background on referring physician computer 20 and consulting physician computer 38. In all other respects, system 10' operates in the same manner as does system 10.

Figure 4:
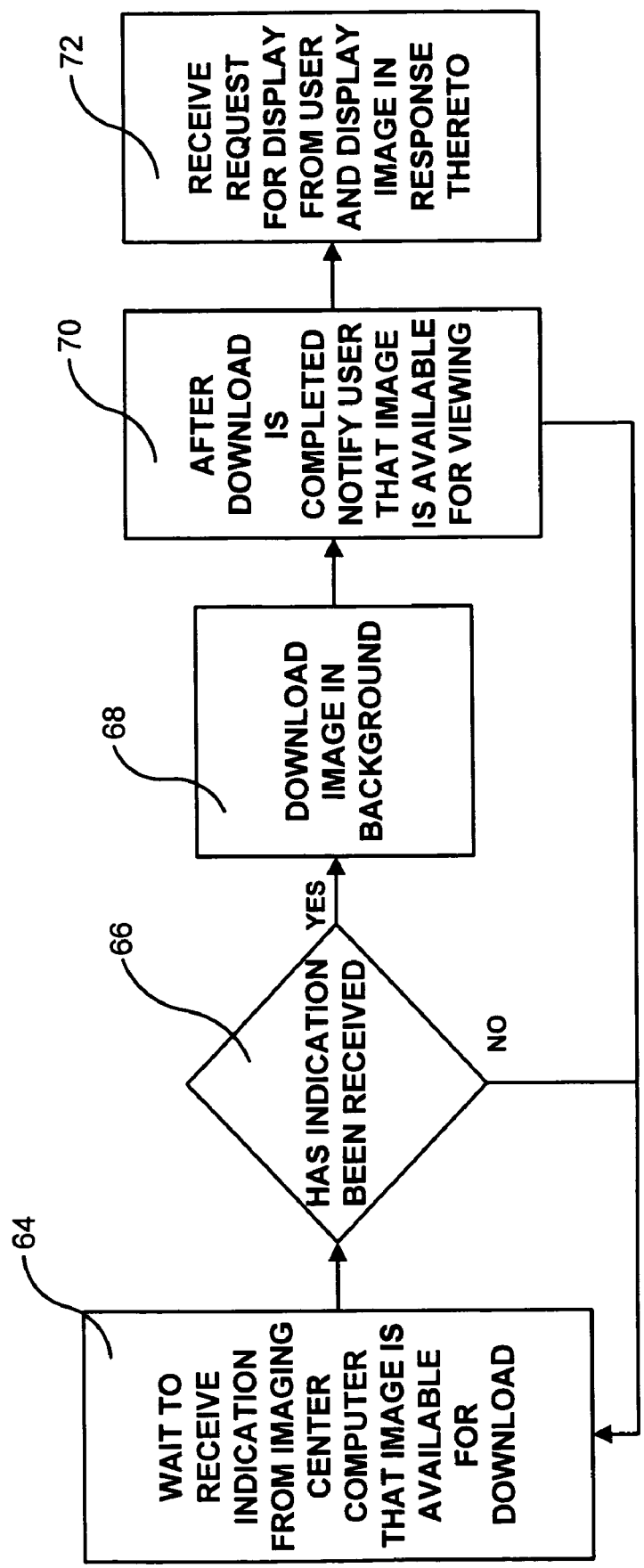
FIG. 4 is flow chart illustrating operation of the system for facilitating the communication of images shown in FIG. 3.

Referring now to FIG. 4, operation of program 22, 40 running on either referring physician computer 20 or consulting physician computer 38 in accordance with system 10' is shown in flow chart form. First, at step 64, program 22, 40 waits to receive an indication from the imaging center computer than an image is available for download. At decision block 66, if it is determined that no image is available for download, program 22, 40 continues to wait for an indication from the imaging center computer. However, if it is determined that an image is available for download, program 22, 40 downloads the image in the background at block 68. After the download is completed, program 22, 40 notifies the user (i.e., either the referring physician or the consulting physician) that an image is available for viewing at block 70. Program 22, 40 also goes back to waiting for an indication from the imaging center computer that another image is available for download. Program 22, 40 then, after receiving a request for display of the image from the user (via a user selectable indicia for example) displays the image to the user at block 72.

The present invention, therefore, provides a system which does not require a user to choose between waiting for an extended period while an image downloads or sacrificing image quality. More specifically, what is desired is a system which provides high quality, images to a user without requiring compression resulting in image degradation and without requiring that a user request to view an image and then wait an unreasonably long time for the requested image to be downloaded.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for facilitating the communication of images, said system comprising:
    a central computer;
    at least one remote computer having a processor, said at least one remote computer being a physician computer in communication with said central computer via a communication link; and
    a program running on said processor;
    wherein said program causes said at least one remote computer to automatically and without user input determine whether an image is available for download from said central computer, and when an image is available for download from said central computer, to automatically and without user input download the image in the background;
    wherein said program, after the download of the image is completed, causes said at least one remote computer to generate and cause to be displayed a notification that the image is ready for display; and
    wherein said program, in response to a request to display the downloaded image, causes said at least one remote computer to display the image.

2. The system of claim 1 wherein said central computer comprises an imaging center computer.

3. The system of claim 1 wherein said at least one remote computer comprises a referring physician computer.

4. The system of claim 3 wherein said at least one remote computer further comprises a consulting physician computer having a processor and wherein a program running on said processor causes the consulting physician computer to determine that an image is available for download only if a request that the image be shared with the consulting physician computer is received from the referring physician computer.

5. The system of claim 1 wherein the image comprises a medical image file plus at least one appended data file.

6. The system of claim 5 wherein the medical image file comprises a Digital Imaging and Communications in Medicine (DICOM) standard image.

7. The system of claim 1 wherein status of the image download by said remote computer is visible to a user of said remote computer.

8. The system of claim 1 wherein status of the image download by said remote computer is invisible to a user of said remote computer.

9. The system of claim 1 further comprising an archive for long-term storage of the image.

10. The system of claim 1 wherein said at least one remote computer comprises a removable storage device onto which the image may be saved.

11. The system of claim 1 wherein said program running on the processor of said at least one remote computer causes said at least one remote computer to automatically and without user input determine whether an image is available for download from said central computer by causing said at least one remote computer to automatically and without user input polling said central computer periodically or from time-to-time to determine whether an image is available for download.

12. The system of claim 1 wherein said program running on the processor of said at least one remote computer causes said at least one remote computer to automatically and without user input determine whether an image is available for download from said central computer by causing said at least one remote computer to automatically and without user input receiving an indication that an image is available for download from said central computer.

13. A system for facilitating the communication of medical images from an imaging center to at least one physician, said system comprising:
an imaging center computer;
a referring physician computer having a processor, said referring physician computer being in communication with said imaging center computer via a communication link; and
a program running on said processor;
wherein said program causes said referring physician computer to automatically and without user input poll said imaging center computer periodically or from time-to-time to determine whether an image is available for download, and when an image is available for download from said imaging center computer, to automatically and without user input download the image in the background;
wherein said program, after the download of the image is completed, causes said referring physician computer to generate and cause to be displayed a notification that the image is ready for display; and
wherein said program, in response to a request to display the downloaded image, causes said referring physician computer to cause the image to be displayed.

14. The system of claim 13 further comprising:
a consulting physician computer having a processor, said consulting physician computer being in communication with said imaging center computer via a communication link; and
a program running on said processor;
wherein said program causes said consulting physician computer to automatically and without user input poll said imaging center computer periodically or from time-to-time to determine whether an image is available for download, and when an image is available for download from said imaging center computer, to automatically and without user input download the image in the background;
wherein said program, after the download of the image is completed, causes said consulting physician computer to generate and cause to be displayed a notification that the image is ready for display; and
wherein said program, in response to a request to display the downloaded image, causes said consulting physician computer to cause the image to be displayed.

15. The system of claim 14 wherein said program running on the processor of said consulting physician computer causes said consulting physician computer to determine that an image is available for download only if a request that the image be shared with the consulting physician computer is received from the referring physician computer.

16. The system of claim 13 wherein the image comprises a medical image file plus at least one appended data file.

17. The system of claim 16 wherein the medical image file comprises a Digital Imaging and Communications in Medicine (DICOM) standard image.

18. The system of claim 13 wherein status of the image download by said referring physician computer is visible to a user of said referring physician computer.

19. The system of claim 13 wherein status of the image download by said referring physician computer is invisible to a user of said referring physician computer.

20. The system of claim 13 further comprising an archive for long-term storage of the image.

21. The system of claim 13 wherein said referring physician computer comprises a removable storage device onto which the image may be saved.

22. A method for facilitating the communication of images, said method comprising the steps of:
determining, automatically and without user input, whether an image is available for download from a central computer;
downloading, when it is determined that an image is available for download, the image in the background of a remote physician computer operating system automatically and without user input;
notifying, after the download is completed, a user that the image is available for viewing on the remote physician computer;
receiving a request for display of the image from the user; and
displaying the image to the user on the remote physician computer.

23. The method of claim 22 wherein the central computer comprises an imaging center computer.

24. The method of claim 22 wherein said downloading, said notifying, said receiving, and said displaying steps are performed by a referring physician computer.

25. The method of claim 24 further comprising the steps of:
receiving, with the central computer, an indication from the referring physician computer that the image should be shared with a consulting physician computer;
making the image available for download by the consulting physician computer; and
performing said downloading, said notifying, said receiving, and said displaying steps with the consulting physician computer.

26. The method of claim 24 wherein status of said downloading step is visible to a user of the referring physician computer.

27. The method of claim 24 wherein status of said downloading step is invisible to a user of the referring physician computer.

28. The method of claim 22 wherein said determining step comprises the step of automatically and without user input polling a central computer periodically or from time-to-time to determine whether an image is available for download.

29. The method of claim 22 wherein said determining step comprises the step of automatically and without user input receiving an indication that an image is available for download from said central computer.

* * * * *